(12) United States Patent
Mogna et al.

(10) Patent No.: US 9,185,927 B2
(45) Date of Patent: Nov. 17, 2015

(54) **BACTERIOCIN-PRODUCING *LACTOBACILLUS PENTOSUS* AND THE USE THEREOF IN FOOD AND PHARMACEUTICAL COMPOSITIONS**

(75) Inventors: Giovanni Mogna, Novara (IT); Gian Paolo Strozzi, Novara (IT); Luca Mogna, Novara (IT)

(73) Assignee: Probiotical S.p.A., Novara (IT)

( * ) Notice: Subject to any disclaimer, the term of this patent is extended or adjusted under 35 U.S.C. 154(b) by 138 days.

(21) Appl. No.: 13/322,795

(22) PCT Filed: May 27, 2010

(86) PCT No.: PCT/IB2010/001290
§ 371 (c)(1),
(2), (4) Date: Mar. 8, 2012

(87) PCT Pub. No.: WO2010/136891
PCT Pub. Date: Dec. 2, 2010

(65) Prior Publication Data
US 2012/0164119 A1 Jun. 28, 2012

(30) Foreign Application Priority Data
May 27, 2009 (IT) .............................. RM2009A0270

(51) Int. Cl.
| C12N 1/20 | (2006.01) |
| A23L 1/30 | (2006.01) |
| A61K 35/747 | (2015.01) |
| C12R 1/225 | (2006.01) |

(52) U.S. Cl.
CPC ............. *A23L 1/3014* (2013.01); *A61K 35/747* (2013.01); *C12R 1/225* (2013.01); *A23Y 2220/65* (2013.01)

(58) Field of Classification Search
None
See application file for complete search history.

(56) References Cited

U.S. PATENT DOCUMENTS 7,125,708 B2 * 10/2006 Wynne et al. .............. 435/252.9

FOREIGN PATENT DOCUMENTS

| WO | WO 03/033681 A2 | 4/2003 |
| WO | WO 2007/003917 A1 | 1/2007 |

OTHER PUBLICATIONS

Delgado et al., Food Microbiology 22 (2005) 521-528.*
Todorov et al. (World Journal of Microbiology and Biotechnology, vol. 20 (2004) 643-650).*
Todorov et al. (Brazilian Journal of Microbiology 38 (2007) 166-172).*
Casey et al., Appl Environ Microbiol. Mar. 2007;73(6):1858-63. Epub Jan. 19, 2007.*
Siggers et al., J. Nutr. 138: 1437-1444, 2008.*
Basu et al., J Clin Gastroenterol. Mar. 2009;43(3):208-13).*
Todorov S.D. et al.: "Screening for bacterioncin-producing lactic acid bacteria from boza, a traditional cereal beverage from Bulgaria Comparison of the bacteriocins", Process Biochemistry, vol. 14, No. 1, Jan. 2, 2006, pp. 11-19.
Torriani S. et al.: Differentiation of *Lactobacillus plantarum*, *L. pentosus*, and *L. paraplantarum* by recA Gene Sequence Analysis and Multiplex PCR Assay with recA Gene-Derived Primers; Applied and Environmental Microbiology, Aug. 2001, pp. 3450-3454.
U.S. Appl. No. 13/254,730, filed Nov. 28, 2011, Bacteria Strains Having a High Anti-Inflammatory Activity.
U.S. Appl. No. 13/255,176, filed Nov. 21, 2011, Oily Suspension Containing Probiotic Bacteria for Paediatric Uses.
U.S. Appl. No. 13/516,579, filed Dec. 17, 2012, Conjugated Linoleic Acid-Producing Strains of Probiotic Bacteria and Use Thereof for the Preparation of a Food, Dietetic or Pharmaceutical Composition.
U.S. Appl. No. 13/583,477, filed Sep. 7, 2012, Composition Comprising Probiotic Bacteria for Use in the Treatment of Immune Disorders.
U.S. Appl. No. 13/806,936, filed Dec. 26, 2012, Use of *Lactobscilli* Inhibiting Gas Products Coliform Bacteria Isolated From Infants Affected by Colic.

* cited by examiner

*Primary Examiner* — Irene Marx
(74) *Attorney, Agent, or Firm* — McCarter & English, LLP; Danielle L. Herritt; Jill Ann Mello

(57) ABSTRACT

The present invention relates to a selected strain of *Lactobacillus pentosus* for use as a medication for the preventive or curative treatment of infections due to Gram-negative bacteria, preferably enterococci, coliforms and *E. coli*.

10 Claims, 1 Drawing Sheet

Fig. 1: *E.coli* ATCC 8739
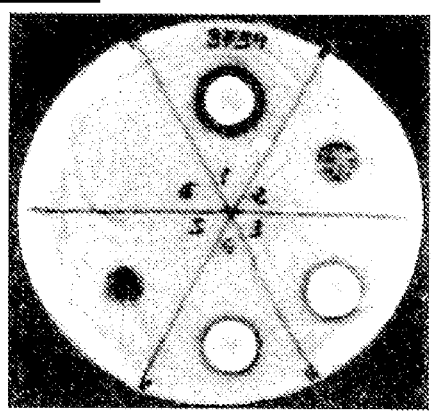
Fig. 2: *E.coli* ATCC 10536
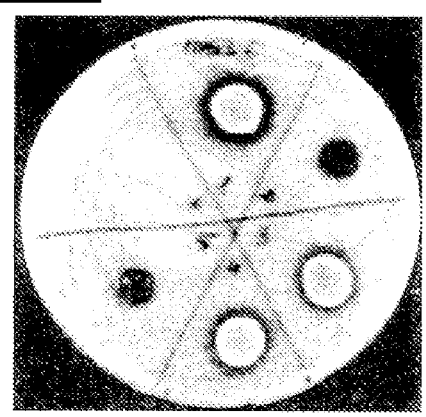
Fig. 3: *E.coli* ATCC 35218
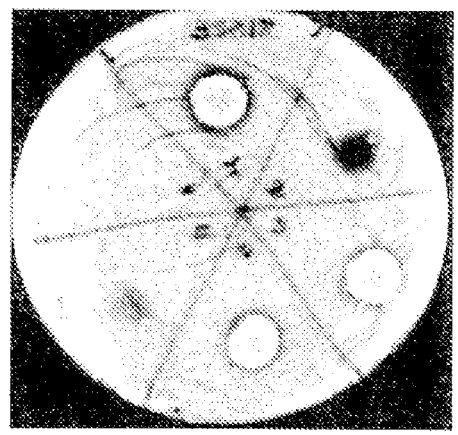
Fig. 4: *E.coli* ATCC 25922
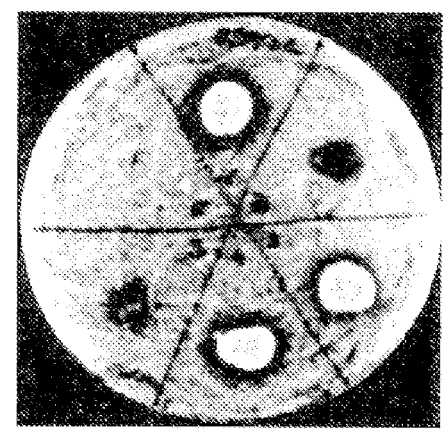

BACTERIOCIN-PRODUCING *LACTOBACILLUS PENTOSUS* AND THE USE THEREOF IN FOOD AND PHARMACEUTICAL COMPOSITIONS

RELATED APPLICATIONS

This application is a 35 U.S.C. §371 national stage filing of International Application No. PCT/IB2010/001290, filed May 27, 2010, which is related and claims priority to Italian Application Serial No.: RM2009A000270, filed May 27, 2009. The entire contents of these applications are explicitly incorporated herein by reference.

The present invention relates to a selected strain of *Lactobacillus pentosus* for use as a medication for the preventive or curative treatment of infections due to Gram-negative bacteria, preferably enterococci, coliforms and *E. coli*.

In particular, the present invention relates to a composition comprising said strain of *Lactobacillus pentosus* for the preparation of a food or pharmaceutical composition for combating, reducing or inhibiting the presence of Gram-negative bacteria, preferably enterococci, coliforms and *E. coli*.

Furthermore, the present invention relates to the use of said selected strain of *Lactobacillus pentosus* for the preparation of a medication for combating, reducing or inhibiting the presence of Gram-negative bacteria, preferably enterococci, coliforms and *E. coli*; in particular for the treatment of infections due to Gram-negative bacteria, preferably enterococci, coliforms and *E. coli*.

Finally, the present invention relates to the use of said selected strain of *Lactobacillus pentosus*, for the preparation of a technological additive to be added to a starter culture for the preparation of dairy products.

It is known that *E. coli* is an example of a widespread Gram-negative bacteria responsible for a large number of bacterial infections, at times also severe ones, such as for example bacterial cystitis, gastroenteritis and gastroenterocolitis.

In general, the infections due to Gram-negative bacteria are treated using drugs such as, for example, antibiotics.

However, over time some Gram-negative bacteria have developed a certain degree of resistance to the drugs normally used and this sometimes limits their use and the results obtained.

Furthermore, in common medical practice, bacterial infections are treated right away by relying on a pharmacological therapy that is as effective as possible. This approach is often adopted without being able to wait for microbiological tests which reveal which bacterium is involved and which antibiotic it is vulnerable to.

One thus proceeds empirically, administering a known antibiotic assumed to be the most effective for the family of bacteria assumed to be at the basis of the infection.

However, the above-described approach implies administering a considerable quantity of drugs, for example antibiotics, without knowing beforehand if such a therapy will lead to the solution of the problem and consequent recovery. Moreover, the possible side effects connected to the administration of antibiotics, which, as is well known, also act on bacterial flora that is positive and useful for the body, should not be overlooked.

Therefore, it is desirable to have a therapy for the preventive or curative treatment of infections due to Gram-negative bacteria which can be used as an alternative to or in combination with traditional drugs in order to overcome the drawbacks deriving from a sometimes indiscriminate use of antibiotics.

It is known that microorganisms are capable of activating a series of defensive systems, such as for example the one regulated by the production of bacteriocins.

The term "bacteriocins" is used to indicate the proteinaceous compounds produced by both Gram-positive and Gram-negative bacteria and endowed with an inhibitory action against bacterial strains which are different from the producer strain, but closely related thereto.

Bacteriocins are proteins produced by lactic bacteria and they show a marked antimicrobial activity by virtue of which they have aroused growing interest, above all in the clinical and technological/food sectors.

Insofar as application in the clinical sector is concerned, bacteriocins represent a valid alternative to antibiotics.

In the food sector, bacteriocins can be used as biopreservatives to control and contain the undesired bacterial population responsible for intoxications and spoilage of the food matrix, for example in dairy products.

Therefore, the use of bacteriocins in the food and pharmaceutical sectors could be a technologically correct and effective tool, to be used in the production of what are defined as "high quality" products, which keep for long periods of time in the absence of any alterations and in complete safety, thus maintaining their intrinsic sensory characteristics.

Finally, a valid application of bacteriocins as antimicrobial substances would involve the use of bacteriocin-producing bacterial cultures as dietary probiotics.

Thus there remains a need to identify and select strains of lactic bacteria which are capable of combating, through a bactericidal action, and/or reducing or inhibiting, through a bacteriostatic action, the presence of Gram-negative bacteria, preferably enterococci, coliforms and *E. coli*.

In particular, there remains a need to identify and select strains of lactic bacteria which are capable of combating, reducing or inhibiting a broad spectrum of Gram-negative bacteria, preferably enterococci, coliforms and *E. coli*, thus enabling them to be validly used in the food or pharmaceutical sector as a total or partial replacement for traditional antibiotics.

Furthermore, there remains a need to identify and select strains of lactic bacteria that can be used together in a mixture thanks to absence, in each selected strain, of an inhibitory action against the other bacteria included in the mixture or already present in the intestinal bacterial flora in the intestines.

The Applicant has identified and selected a strain of *Lactobacillus pentosus* which is able to provide a suitable response to the above-mentioned needs.

For this reason, the subject of the present invention is a strain of *Lactobacillus pentosus*, deposited with the DSMZ Institute in Germany under DSM No. 21980, for use as a medication for the preventive or curative treatment of infections due to Gram-negative bacteria, preferably enterococci, coliforms and *E. coli*.

A further subject of the present invention is a composition comprising said *Lactobacillus pentosus* DSM No. 21980 for the preparation of a food or pharmaceutical composition for combating, reducing or inhibiting the presence of Gram-negative bacteria, preferably enterococci, coliforms and *E. coli*.

A further subject of the present invention is the use of said strain *Lactobacillus pentosus* DSM No. 21980 to prepare a medication for combating, reducing or inhibiting the presence of Gram-negative bacteria, preferably enterococci, coliforms and *E. coli*; in particular for the treatment of infections due to Gram-negative bacteria, preferably enterococci, coliforms and *E. coli*.

A further subject of the present invention is the use of said strain *Lactobacillus pentosus* DSM No. 21980 to prepare a technological additive to be added to a starter culture for the preparation of dairy products.

Other preferred embodiments of the present invention will become apparent from the detailed description that follows.

Table 1 shows an experimental test in which the inhibitory activity of a group of bacterial strains against *E. coli* was tested. In Table 1 it is shown as follows: (−) no halo (no inhibition); (+)halo of 1-2 mm→(*) numerous colonies of *E. coli* inside the spot; (++)halo of 3-5 mm→(**) a few colonies of *E. coli* inside the spot; (+++) halo greater than 5 mm→ (***) no colony of *E. coli* (maximum inhibition).

TABLE 1

| Tested strain | Culture medium | Final pH of broth culture | Entire sample 10 μl of broth culture | Washed cells | Filtered broth |
|---|---|---|---|---|---|
| L. pentosus LPS01 DSM 21980 | MRS | 3.87 | +++ | +++ | ** |
|  | LaptG | 3.98 |  |  | ** |
| L. rhamnosus LR06 DSM 21981 | MRS | 4.04 | ++ | ++ | * |
|  | LaptG | 4.40 | + |  | * |
| L. reuteri ATCC 55730 | MRS | 4.15 | −/+ | + | * |
|  | LaptG | 4.33 | + |  | * |
| L. rhamnosus GG | MRS | 4.12 | − | − | − |
|  | LaptG | 4.50 | − |  |  |
| L. fermentum LF5 | MRS | 4.12 | ++ | + | −/* |
|  | LaptG | 4.23 | ++ |  | −/* |
| L. plantarum LP02 | MRS | 4.00 | +++ | ++ | * |
|  | LaptG | 4.02 | ++ |  | * |
| L. plantarum ID 094 | MRS | 3.96 | ++ | ++ | * |
|  | LaptG | 3.89 | ++ |  | * |
| L. plantarum LP01 | MRS | 3.87 | ++ | ++ | * |
|  | LaptG | 3.94 | ++ |  | * |
| L. plantarum ID 126 | MRS | 3.79 | ++ | ++ | * |
|  | LaptG | 3.86 | ++ |  | * |
| L. casei sub. paracasei LPC08 | MRS | 4.48 | − | − | − |
|  | LaptG | 4.95 | − |  |  |
| L. acidophilus LA02 | MRS | 3.94 | − | − | − |
|  | LaptG | 3.66 | − |  |  |
| L. lactis sub. cremoris NS01 | MRS | 4.35 | + | + | − |
|  | LaptG | 4.05 | + |  | − |
| S. thermophilus FP4 | MRS | 4.86 | − | − | − |
|  | LaptG | 4.23 | − |  |  |
| Reuterin ATCC 53608 |  |  | + |  |  |
| Reuflor ™ |  |  | + |  |  |
|  | MRS broth | 4.06 | − |  |  |
|  | M17 broth | 4.02 | − |  |  |
|  | LaptG broth | 3.90 | − |  |  |
|  | H₂O | / | − |  |  |

Table 2 shows an inhibition test.

TABLE 2

|  | LR06 | LPS01 | LP01 |
|---|---|---|---|
| LR06 | − | − | − |
| LPS01 | − | − | − |
| LP01 | − | − | − |

Table 3 shows a gastro-resistance test.

TABLE 3

| Strain | Parameters evaluated | % survival Contact time (minutes) | | |
|---|---|---|---|---|
|  |  | 5' | 30' | 60' |
| Lactobacillus pentosus DSM 21980 (LPS01) | Human gastric juice | 84 | 55 | 36 |
|  | Simulated gastric juice | 90 | 26 | 15 |
|  | Simulated pancreatic secretion | 93 | 86 | 72 |
|  | Human bile (in culture medium) |  |  | 85 |
|  | Biliary salts (in culture medium) |  |  | 57 |
| Lactobacillus plantarum DSM 9943 | Human gastric juice | 81 | 61 | 40 |
|  | Simulated gastric juice | 88 | 30 | 20 |
|  | Simulated pancreatic secretion | 89 | 83 | 79 |
|  | Human bile (in culture medium) |  |  | 97 |
|  | Biliary salts (in culture medium) |  |  | 63 |
| Lactobacillus rhamnosus ATCC 53103 | Human gastric juice | 88 | 60 | 25 |
|  | Simulated gastric juice | 90 | 30 | 19 |
|  | Simulated pancreatic secretion | 88 | 80 | 73 |
|  | Human bile (in culture medium) |  |  | 84 |
|  | Biliary salts (in culture medium) |  |  | 55 |

FIG. 1 shows the test of growth inhibition of *E. coli* ATCC 8739 by the strain *Lactobacillus pentosus* LPS 01, DSM 21980.

FIG. 2 shows the test of growth inhibition of *E. coli* ATCC 10536 by the strain *Lactobacillus pentosus* LPS 01, DSM 21980.

FIG. 3 shows the test of growth inhibition of *E. coli* ATCC 35218 by the strain *Lactobacillus pentosus* LPS 01, DSM 21980.

FIG. 4 shows the test of growth inhibition of *E. coli* ATCC 25922 by the strain *Lactobacillus pentosus* LPS 01, DSM 21980.

The Applicant has identified and selected a strain of *Lactobacillus pentosus* from natural ensiled maize using the *lactobacillus* isolation technique, known to experts in the field.

The strain was deposited with the DSMZ (Deutsche Sammlung von and Zellkulturen GmbH; Inhoffenstr. 7B, D-38124 Braunschweig) in Germany on Nov. 14, 2008, by Probiotical S.p.A., Novara—Italy, under the following filing number: *Lactobacillus pentosus* DSM No. 21980 (LPS01). The strain DSM 21980 was deposited in accordance with the Treaty of Budapest.

In a preferred embodiment, the *Lactobacillus pentosus* DSM No. 21980 (LPS01) is indicated for the preventive or curative treatment of recurring (recurrent) infections due to Gram-negative bacteria, preferably enterococci, coliforms and *E. coli*.

In another preferred embodiment, the *Lactobacillus pentosus* DSM No. 21980 (LPS01) is indicated for the preventive or curative treatment of gastroenteritis or gastroenterocolitis, preferably for the preventive or curative treatment of diarrheic discharges and consequent dehydration, nausea, diarrhea, abdominal cramps accompanied by fever and physical weakness.

The selected and isolated strain was characterised and classified based on the sugar fermentation profile (API 50 CHL bioMérieux). The species was confirmed by species-specific PCR amplification (Torriani S., Felis G. E., Dellaglio F., *Differentiation of Lactobacillus plantarum, L. pentosus, and L. paraplantarum by recA Gene Sequenze Analysis and Multiplex PCR Assay with recA Gene-Derived Primers*. Appl Environ Microbiol. August 2001; 3450-3454).

The strain was biotyped using the PFGE (Pulsed Field Gel Electrophoresis) technique, (Tynkken S., Satokari R., Saarela M., Mattila-Sandholm T., Saxelin M. *Comparison of Ribotyping, Randomly Amplified Polymorphic DNA Analysis, and Pulsed-Field Gel Electrophoresis in Typing of Lactobacillus rhamnosus and L. casei strains*. Appl And Envirom Microb. September 1999; 3908-3914).

The Applicant has tested the anti-*E. coli* activity of the above-mentioned *Lactobacillus pentoses* DSM No. 21980, which was placed in direct contact with the following *E. coli*: ATCC 35218, ATCC 10536, ATCC 8739, and ATCC 25922.

However, in order to obtain comparative results, other strains of probiotic lactic bacteria were also tested, as stated below.

1) *Lactobacillus reuteri* ATCC 53608, present as the sole microbial ingredient of two different commercially available products, namely Reuterin (Noos) and Reuflor (Italchimici).

The products mentioned in 1 were subjected to assay as the reference positive sample, given the known ability of the strain ATCC 53608, present in the two formulations, to produce a bacteriocin (called reuterin) which is active against Gram-negative bacteria.

Clearly, in order to avoid any type of direct action of the excipients present in the formulations of the two products, the microorganism ATCC 53608 was first isolated and then cultivated in a culture broth and subsequently subjected to assay.

2) *L. rhamnosus* DSM No. 21981 (LR06) as nother strain of interest. The strain was deposited with the DSMZ (Deutsche Sammlung von Mikroorganismen and Zellkulturen GmbH; Inhoffenstr. 7B, D-38124 Braunschweig) in Germany on Nov. 14, 2008, by Probiotical S.p.A., Novara—Italy, under the following filing number: *Lactobacillus rhamnosus* DSM No. 21981 (LR06). The strain DSM 21981 was deposited in accordance with the Treaty of Budapest.

3) *Lactobacillus fermentum* CNCM 1-789 (LF5), active against vaginal *Candida*, and for that reason considered a good candidate in the production of bacteriocins with a broad spectrum of action.

4) *Lactobacillus rhamnosus* GG, ATCC 53103, one of the probiotics best known and most studied in the world as an effective intestinal coloniser.

5) *Lactobacillus plantarum* LMG P-21020, LMG P-21021, LMG P-21022 and LMG P-21023. The four above-mentioned strains, LMG P-21020, LMG P-21021, LMG P-21022 and LMG P-21023, have an ability to produce bacteriocins (called plantaricins) with an anti-bacterial action. The comparison between the strain of the present invention and the 4 strains of *Lactobacillus plantarum* LMG P-21020, LMG P-21021, LMG P-21022 and LMG P-21023 serves to demonstrate the quantity of bacteriocins produced, operating conditions being equal.

6) *Lactobacillus casei* sub. *paracasei* LPC08, DSM 21718, used as a negative reference sample.

7) *Lactobacillus acidophilus* DSM No. 21717 (LA02), used as a negative reference sample.

8) *Lactobacillus lactis* sub. *cremoris* DSM No. 19072 (NS01), used as a producer of Nisin, which is known to be a bacteriocin with a broad spectrum of action (for example, effective against *Listeria* and *Clostridia*).

9) *Streptococcus themophilus* DSM No. 18616 (FP4), used as a negative reference sample.

The target strains are represented by *E. coli*: ATCC 35218, ATCC 10536, ATCC 8739, and ATCC 25922, in lyophilized form, and having a load of at least $1 \times 10^8$ CFU/g.

Each strain of *E. coli* was reconstituted with 1 ml of physiological solution (NaCl 0.8%) and used in a proportion of 100 µl per Petri dish containing 12-15 ml of agarized LaptG culture medium. 1 liter of LaptG culture broth has: Bacto Pepton 15 g, Bacto Tryptone 10 g, Glucose 10 g, Yeast Extract 10 g, Tween 80 1 g, distilled water to 1000 ml, pH 6.5-6.6. For the medium in the solid phase (agarized), 15 g of Bacto Agar is added.

Both media (broth and agar) are sterilized at 121° C./15 minutes (Font De Valdez, G, and coll.: *Influence of the recovery medium on the viability of injured freeze-dried lactic acid bacteria* Milchwissenschaft 40 (9) 518-520 (1985). The Petri dishes were prepared with hot agarized Laptg medium and allowed to solidify under a laminar flow hood. Subsequently, 100 µl of the target strain was evenly distributed over the surface of the Laptg medium using a sterile spatula. Before being incubated, the Petri dishes thus prepared were dried under the laminar flow hood. The results of the inhibition assay are shown in table 1.

The *Lactobacilli* were cultivated in a liquid MRS medium (broth) and LaptG broth, whereas the Lactococci were cultivated in a liquid M17 medium (broth) and LaptG broth. The ingredients and compositions of the culture media are known to experts in the field.

All the bacteria were inoculated at a rate of 1%, starting from the mother culture, and incubated at 37° C. for 16-18 hours in a thermostated bath.

At the end of incubation, the final pH value of the broth culture was measured (see column in Table 1).

It is important to determine the quantity of lactic acid produced by individual bacteria as it is desired to verify that said acidity is not the only parameter responsible for inhibiting the growth of *E. coli*.

At the end of incubation, an aliquot of each broth culture was centrifuged at 5000 rpm/5 min to give an exhausted culture broth and a pellet of cells. The exhausted culture broth was filtered using syringe filters with 0.22 µm pore size and also subjected to testing. Subsequently, the cell pellet was washed once in sterile water to eliminate the residues of culture medium. The washed cell pellet was then resuspended in physiological solution so as to obtain a turbidity of 0.5 based on the McFarland scale. This value makes it possible to start from an initial quantity of cells that is equal for all the tested bacteria.

Prior to the inhibition assay, the position of the respective spots that will be subjected to testing is marked on the bottom of the Petri dishes prepared with the target strain on an LaptG agar base.

10 µl of each bacterial broth culture is spotted onto the surface of the dish seeded with the target strain.

The following are also submitted to analysis:
a) The washed bacterial suspensions. The data in Table 1 (see washed cells column) show that the production of bacteriocin occurs during the replication metabolism of the tested bacteria. This demonstrates that the strain DSM 21980, to which the present invention relates, is capable of inhibiting, combating and/or reducing the growth of *E. coli*.

Therefore, the lyophilized strain DSM 21980, once reconstituted and in a condition to produce its basal metabolism, will be capable of inhibiting, combating and/or reducing the growth of *E. coli*.

b) The exhausted culture broths deriving from the various bacteria. The data in Table 1 (see filtered broth column) indicate how much bacteriocin is present in the culture broth. This demonstrates that the bacteriocin is exogenous, active and present in sufficient quantities to inhibit *E. coli*.

c) The culture broths MRS, M17 and LaptG acidified by adding lactic acid until reaching a pH near the final pH of the culture broths (3.9-4.5). The data in Table 1 (see bottom 4 lines) show that the action of inhibition of *E. coli* is largely due to the production of bacteriocins and not to the pH of the medium.

d) Sterile water.

The dishes thus prepared are incubated in a thermostat at 37° C./24 hours.

At the end of incubation there will be uniform growth of the target strain across the entire dish, except in the areas where bacteriocin is present. The data are shown in Table 1.

As confirmation of the results shown in Table 1, a practical example is given below in relation to the test of growth inhibition of *E. coli* by the strain *Lactobacillus pentosus* LPS 01, DSM 21980.

In the four images shown below (FIGS. 1-4) it may be noted that:

the Petri dish containing the agarized LaptG medium had a portion of the target strain *E. coli* distributed over its surface;

the symbols and black lines delimit the sectors pertaining to the various types of samples tested;

the "spot" consists of 10 μl of each sample tested. It should be pointed out that in the case of a sample consisting of complete broth cultures the spot appears more opaque compared to the remaining portions of the dish, an indication that bacterial multiplication has taken place;

The inhibition halo, the dark portion present in each dish in sectors 1-2-3-4-5, where the target strain did not multiply because of the bacteriocin's action, is directly proportional the quantity thereof.

The various sectors are described below:

Sector 1: effect of inhibition by the complete broth culture (cells plus LaptG culture medium) of the strain *Lactobacillus pentosus* LPS 01, DSM 21980.

Sector 2: effect of inhibition by the filtered broth of the strain *Lactobacillus pentosus* LPS 01, DSM 21980, after the strain itself was allowed to grow.

It may be inferred from the presence of the dark halo that the bacteriocin produced is exogenous because it is secreted by the cells. The bacteriocin produced remains active in the culture broth.

Sector 3: effect of inhibition by the complete broth culture (cells plus LaptG culture medium) of the strain *L. rhamnosus* DSM No. 21981 (LR06).

Sector 4: effect of inhibition by the complete broth culture (cells plus LaptG culture medium) of the strain *L. reuteri* ATCC 53608.

Sector 5: effect of inhibition by the filtered LaptG broth in which the strain *Lactobacillus pentosus* DSM 21980 (LPS 01) grew, after the pH was neutralized to 6.8 by adding 0.1N soda, to rule out the possibility that the action exerted on the target was determined solely by the acidity of the medium (culture broth).

Sector 6: effect of inhibition of the LaptG culture broth as such. In this case the formation of a halo is not observed since the culture broth possesses no ingredients with an inhibitory action.

The four images relate to trials conducted under the same operating conditions but using a different *E. coli* strain each time: *E. coli* ATCC 8739 (FIG. 1), ATCC 10536 (FIG. 2), ATCC 35218 (FIG. 3) and ATCC 25922 (FIG. 4).

Based on the above-described trials it may be inferred that the strain *L. pentosus* DSM No. 21980 (LPS 01) showed an excellent inhibitory ability against all the *E. coli* strains, ATCC 8739, ATCC 10536, ATCC 35218 and ATCC 25922, in virtue of its ability to produce a more effective bacteriocin in large quantities.

Based on the results reported above, it may be inferred that the strain *Lactobacillus pentosus* DSM No. 21980 (LPS01) has a broad spectrum of action, since it is capable of combating, inhibiting and reducing the growth of all four *E. coli* strains tested.

Furthermore, based on the results shown in Table 1 and in FIGS. 1-4, it may be inferred that the strain *L. pentosus* DSM No. 21980 (LPS 01) is capable of combating, through a bactericidal action, and/or reducing or inhibiting, through a bacteriostatic action, the presence of Gram-negative bacteria, preferably enterococci, coliforms and *E. coli*.

Furthermore, the Applicant tested the strain *L. pentosus* DSM No. 21980 (LPS 01), to which the present invention relates, against other probiotic strains taken individually, namely, *Lactobacillus rhamnosus* DSM No. 21981 (LR06) and *Lactobacillus plantarum* No. LMG P-21021 (LP01). This test had the aim of verifying whether the production of bacteriocin by *L. pentosus* DSM No. 21980 (LPS 01) can in some way inhibit the other bacteria *Lactobacillus rhamnosus* DSM No. 21981 (LR06) and *Lactobacillus plantarum* No. LMG P-21021 (LP01) during the growth thereof because of the presence of bacteriocin.

Accordingly, a test was performed in which the strains *Lactobacillus rhamnosus* DSM No. 21981 (LR06) and *Lactobacillus plantarum* No. LMG P-21021 (LP01) were crossed, exactly as in the assay described above, with the pathogen *E. coli*.

The data relative to the strains used *Lactobacillus pentosus* DSM No. 21980 (LPS01); *Lactobacillus rhamnosus* DSM No. 21981 (LR06) and *Lactobacillus plantarum* No. LMG P-21021 (LP01) are shown in Table 2.

In Table 2, that no halo (no inhibition) is present is shown with (−). As may be seen from Table 2, no bacteria showed inhibitory abilities against the other crossed probiotic bacteria.

The strain *Lactobacillus pentosus* DSM No. 21980 (LPS01) does not interfere with other strains of probiotic bacteria or with beneficial bacterial flora.

A preferred embodiment of the present invention relates to a composition comprising the strain *Lactobacillus pentosus* DSM No. 21980 (LPS01) for use as a medication for the preventive or curative treatment of infections due to Gram-negative bacteria, preferably by enterococci, coliforms and *E. coli*.

Another preferred embodiment of the present invention relates to a composition for use as a medication for the preventive or curative treatment of recurring infections (recurrent infections) due to Gram-negative bacteria, preferably enterococci, coliforms and *E. coli*.

Preferably, said composition is indicated for the preventive or curative treatment of gastroenteritis or gastroenterocolitis. Even more preferably it is indicated for the preventive or curative treatment of diarrheic discharges and consequent dehydration, nausea, diarrhea, abdominal cramps accompanied by fever and physical weakness.

In the above-mentioned compositions the strain *Lactobacillus pentosus* DSM No. 21980 (LPS01) can be alive or dead or, alternatively, the cellular components thereof can be present.

In a preferred embodiment, the strain *Lactobacillus pentosus* DSM No. 21980 (LPS01), in the form of live or dead bacteria or, alternatively, the cellular components thereof, can be used to prepare a dietary composition which has valid application, as a technological additive, in the dairy industry. Said dietary composition is added to a starter culture for the preparation of dairy products.

In a preferred embodiment, the above-mentioned compositions may also comprise the strain *Lactobacillus rhamnosus* DSM No. 21981 (LR06) and/or the strain *Lactobacillus pen-* tosus DSM No. 21980 (LPS01) in association with the strain *Lactobacillus pentosus* DSM No. 21980 (LPS01).

The compositions contain the strain *Lactobacillus pentosus* DSM No. 21980 (LPS01) as live or dead bacteria or the cellular components thereof in a quantity of between $1\times10^6$ and $1\times10^{11}$ CFU/g, relative to the total weight of the composition, preferably between $1\times10^8$ and $1\times10^{10}$ CFU/g.

In a preferred embodiment, the above-mentioned compositions contain the strain as live or dead bacteria or the cellular components thereof in a quantity of between $1\times10^6$ and $1\times10^{11}$ CFU/dose, preferably between $1\times10^8$ and $1\times10^{10}$ CFU/dose. The doses may be for example 1 g, 3 g, 5 g and 10 g.

The compositions can also contain additives and co-formulants that are acceptable from a dietary and pharmaceutical point of view.

The compositions can include vitamins, e.g. folic acid, vitamin $B_{12}$, riboflavin, pyridoxal phosphate, vitamin E and ascorbic acid; antioxidants, e.g. polyphenols, flavanoids, proanthocyanidins and catechins; amino acids, e.g. glutamine and methionine; minerals, e.g. selenium, copper, magnesium and zinc; active substances of plant origin, preferably in the form of a dry extract, such as cranberry, *Echinacea*, grapefruit seed extract, equisetum, bearberry, rosemary and propolis.

In a preferred embodiment, the compositions also contain at least one substance having prebiotic properties in a quantity of between 1 and 30% by weight, relative to the total weight of the composition, preferably between 5 and 20% by weight.

Said prebiotic substances include fructo-oligosaccharides (FOS), xylo-oligosaccharides (XOS), galacto-oligosaccharides, inulin, arabino-galactanes and gluco-oligosaccharides.

In a preferred embodiment, the strain *Lactobacillus pentosus* DSM No. 21980 (LPS01) is induced to produce bacteriocin on a massive scale via stimulation of the anti-*E. coli* bacteriocin. The bacteriocin obtained is extracted from the massive production described above so as to obtain the bacteriocin of the present invention as such. The latter may be used in the above-described compositions in order to combat (through bactericidal action) and/or reduce or inhibit (through bacteriostatic action) the presence of Gram-negative bacteria, preferably enterococci, coliforms and *E. coli*.

Furthermore, gastro-resistance tests were set up in order to evaluate the ability of the strain *Lactobacillus pentosus* DSM No. 21980 (LPS 01) to reach the intestine in numbers large enough to colonize the intestinal wall. The tests were performed following the methods known in the art and cited in the appended list of references (references 1-5). The tests were set up considering the strain *Lactobacillus plantarum* DSM 9843 as a positive reference, since it is a strain belonging to the *Plantarum* family of human origin, capable of colonizing the intestine. Furthermore, the strain *Lactobacillus rhamnosus* ATCC 53103 (LGG) was tested since it is a well-studied, well-characterized probiotic *lactobacillus*. The data are shown in Table 3.

Table 3 shows the percentage of survival of probiotic strains versus two different types of gastric juices and a pancreatic secretion simulated after different contact times (5', 30' and 60') at 37° C.

The results of survival versus biliary secretion were obtained by comparing the number of colonies growing in a culture medium with or without the addition of biliary salts or human bile.

Based on the data provided in Table 3, it may be inferred that the strain *Lactobacillus pentosus* DSM No. 21980 (LPS01) shows good survival in gastroduodenal transit, wholly comparable to that of the reference strain *Lactobacillus plantarum* DSM No. 9843. Therefore, the strain *Lactobacillus pentosus* DSM No. 21980 (LPS01) is able to pass the gastrointestinal barrier and colonise the intestinal tract.

The data provided in Table 1, FIG. 1-4, Table 2 and Table 3 support the use of the strain *Lactobacillus pentosus* DSM No. 21980 (LPS01) in the food or pharmaceutical sector as a total or partial replacement for traditional antibiotics in the preventive or curative treatment of infections due to Gram-negative bacteria.

REFERENCES

1. Human gastric juice—Met. Int. 006 (DAS)
   Reference: Del Piano M., Morelli L., Strozzi G P., Allesina S., Barba M., Deidda F., Lorenzini P., Ballare M., Montino F., Orsello M., Sartori M., Garello E., Carmagnola S., Pagliarulo M., Capurso S.: Probiotics: from research to consumer. Dig Liver Dis. 2006 December; 38 Suppl 2:S248-55. Review.
2. Artificial gastric juice—Met. Int. 022 (DAS)
   Reference: Charteris W P. et al. Development and application of an in vitro methodology to determine the transit tolerance of potentially probiotic *Lactobacillus* and *Bifidobacterium* species in the upper human gastrointestinal tract. J Appl Microbiol. 1998 May; 84 (5):759-68.
3. Simulated pancreatic juice—Met. Int. 023 (DAS)
   Reference: Charteris W P. et al. Development and application of an in vitro methodology to determine the transit tolerance of potentially probiotic *Lactobacillus* and *Bifidobacterium* species in the upper human gastrointestinal tract. Journal of Applied Microbiology 1998 May; 84 (5):759-68
   Del Piano M., Strozzi G P., Barba M.; Allesina S.; Deidda F. Lorenzini P., Morelli L.; Carmagnola S.; Pagliarulo M.; Balzarini M.; Ballare M.; Orsello M.; Montino F.; Sartori M.; Garello E.; Capurso L. In Vitro Sensitivity of Probiotics to Human Pancreatic Juice. Journal of Clinical Gastroenterology. 2008 Aug. 5.
4. Human bile—Met. Int. 024 (DAS)
   Reference: Del Plano M., Morelli L., Strozzi G P., Allesina S., Barba M., Deidda F., Lorenzini P., Ballare M., Montino F., Orsello M., Sartori M., Garello E., Carmagnola S., Pagliarulo M., S. Capurso: Probiotics: from research to consumer. Dig Liver Dis. 2006 December; 38 Suppl 2:S248-55. Review.
5. Bile Salts—Met. Int. 024 (DAS)
   Reference: Charteris W P. et al. Development and application of an in vitro methodology to determine the transit tolerance of potentially probiotic *Lactobacillus* and *Bifidobacterium* species in the upper human gastrointestinal tract. J Appl Microbiol. 1998 May; 84 (5):759-68.

The invention claimed is:

1. A method for treating gastroenteritis in a subject in need thereof, the method comprising orally administering to the subject an effective amount of isolated bacterial strain *Lactobacillus pentosus* LPS 01, deposited on Nov. 14, 2008 with Deutsche Sammlung von Mikroorganismen und Zellkulturen GmbH (DSMZ) under Accession Number No. DSM 21980, such that said gastroenteritis is treated.

2. The method of claim 1, wherein the gastroenteritis causes diarrhea discharges with subsequent dehydration, nausea or abdominal cramps.

3. The method of claim 1, wherein the effective amount is between $10^6$ and $10^{11}$ CFU.

4. The method of claim 1, wherein the isolated bacterial strain *Lactobacillus pentosus* LPS 01 comprises live bacterial cells.

5. The method of claim 1, further comprising administering isolated bacterial strain *Lactobacillus rhamnosus* LR06, deposited on Nov. 14, 2008 with Deutsche Sammlung von Mikroorganismen und Zellkulturen GmbH (DSMZ) under Accession Number No. DSM 21981.

6. A method for treating gastroenteritis in a subject in need thereof, the method comprising orally administering to the subject a pharmaceutical composition comprising an effective amount of isolated bacterial strain *Lactobacillus pentosus* LPS 01, deposited on Nov. 14, 2008 with Deutsche Sammlung von Mikroorganismen und Zellkulturen GmbH (DSMZ) under Accession Number DSM 21980, such that said gastroenteritis is treated.

7. The method of claim 6, wherein the gastroenteritis causes diarrhea discharges with subsequent dehydration, nausea or abdominal cramps.

8. The method of claim 6, wherein the effective amount is between $10^6$ and $10^{11}$ CFU.

9. The method of claim 6, wherein the isolated bacterial strain *Lactobacillus pentosus* LPS 01 comprises live bacterial cells.

10. The method of claim 6, wherein the pharmaceutical composition further comprises isolated bacterial strain *Lactobacillus rhamnosus* LR06, deposited on Nov. 14, 2008 with Deutsche Sammlung von Mikroorganismen und Zellkulturen GmbH (DSMZ) under Accession Number No. DSM 21981.

* * * * *